(12) United States Patent
Park (10) Patent No.: US 9,724,142 B2
(45) Date of Patent: Aug. 8, 2017

(54) FEMORAL LESSER TROCHANTER SECURING DEVICE FOR FIRMLY SECURING THE LESSER TROCHANTER AND THE SURROUNDS AND STABLY STRENGTHENING THE SAME SO AS TO ALLOW ARTIFICIAL HIP REPLACEMENT SURGERY (76) Inventor: Jeesun Park, Seongnam-si (KR)

( * ) Notice: Subject to any disclaimer, the term of this patent is extended or adjusted under 35 U.S.C. 154(b) by 394 days.

(21) Appl. No.: 13/813,235

(22) PCT Filed: Jun. 20, 2011

(86) PCT No.: PCT/KR2011/004473
§ 371 (c)(1),
(2), (4) Date: Jan. 30, 2013

(87) PCT Pub. No.: WO2012/020915
PCT Pub. Date: Feb. 16, 2012

(65) Prior Publication Data
US 2013/0138105 A1    May 30, 2013

(30) Foreign Application Priority Data
Aug. 13, 2010  (KR) .................. 10-2010-0078141

(51) Int. Cl.
*A61B 17/80* (2006.01)
*A61B 17/74* (2006.01)
(Continued)

(52) U.S. Cl.
CPC .......... *A61B 17/8061* (2013.01); *A61B 17/74* (2013.01); *A61B 17/82* (2013.01);
(Continued)

(58) Field of Classification Search
CPC ........ A61F 2/30739; A61F 2002/30578; A61F 2/36; A61F 2002/30741; A61B 17/74; A61B 17/82; A61B 17/8061
See application file for complete search history.

(56) References Cited

U.S. PATENT DOCUMENTS 4,988,350 A *  1/1991  Herzberg ............. A61B 17/746
                                                      606/65
6,338,734 B1 * 1/2002  Burke .................... A61B 17/74
                                                      606/280

(Continued)

FOREIGN PATENT DOCUMENTS

JP      09-168548 A       6/1997
JP      09168548 A  *    6/1997  ......... A61B 17/8061
(Continued)

OTHER PUBLICATIONS

International Search Report for PCT/KR2011/004473 mailed Feb. 15, 2012 from Korean Intellectual Property Office.

*Primary Examiner* — Christopher Beccia
(74) *Attorney, Agent, or Firm* — Paratus Law Group, PLLC (57) ABSTRACT Provided are a lesser trochanter securing device and an artificial joint device. The device includes a basket portion which covers a lesser trochanter, and a buttress plating portion which is joined to a lower edge of the basket portion, extends toward a femoral shaft and is secured and joined to the femoral shaft.

8 Claims, 4 Drawing Sheets (51) Int. Cl.
*A61B 17/82* (2006.01)
*A61F 2/30* (2006.01)
*A61F 2/36* (2006.01)

(52) U.S. Cl.
CPC ............ *A61F 2/30739* (2013.01); *A61F 2/36* (2013.01); *A61F 2002/30578* (2013.01); *A61F 2002/30741* (2013.01)

(56) References Cited

U.S. PATENT DOCUMENTS

| | | | |
|---|---|---|---|
| 6,338,743 | B1 | 1/2002 | Dusemund et al. |
| 2005/0240187 | A1* | 10/2005 | Huebner ................ A61B 17/80 606/71 |
| 2011/0137314 | A1* | 6/2011 | Kuster .................. A61B 17/74 606/70 |

FOREIGN PATENT DOCUMENTS

| | | |
|---|---|---|
| KR | 10-0904088 B1 | 6/2009 |
| KR | 10-0909580 B1 | 7/2009 |
| KR | 10-0917715 B1 | 9/2009 |

\* cited by examiner

FEMORAL LESSER TROCHANTER SECURING DEVICE FOR FIRMLY SECURING THE LESSER TROCHANTER AND THE SURROUNDS AND STABLY STRENGTHENING THE SAME SO AS TO ALLOW ARTIFICIAL HIP REPLACEMENT SURGERY

CROSS REFERENCE TO PRIOR APPLICATIONS

This application is a National Stage Patent Application of PCT International Patent Application No. PCT/KR2011/004473 (filed on Jun. 20, 2011) under 35 U.S.C. §371, which claims priority to Korean Patent Application No. 10-2010-0078141 (filed on Aug. 13, 2010), which are all hereby incorporated by reference in their entirety.

TECHNICAL FIELD

The present invention relates to prostheses, and more particularly, to a lesser trochanter securing device for orthopedic surgery, which is attached to comminuted fractures of a femoral lesser trochanter and surrounds thereof.

BACKGROUND ART

Anatomical terminology used in the detailed description is based on the Color Atlas of Anatomy by Rochen and Yokochi.

SUMMARY OF INVENTION

Technical Problem

A technical problem to be solved by the present invention is to provide a lesser trochanter securing device that can expand the application of an artificial hip joint replacement surgery.

A technical problem to be solved by the present invention is to provide an artificial joint for the application of an artificial joint replacement surgery, which includes a lesser trochanter securing device for easily reducing and firmly fixing a lesser trochanter fracture area.

Solution to Problem

A lesser trochanter securing device according to an embodiment of the present invention includes a basket portion and a buttress plating portion. The basket portion covers and buttresses a lesser trochanter and a part of a bone around a neck of a femoral stem inserted into a femoral medullary canal, and easily recovers and three-dimensionally secures a fracture area so as to prevent refracture. The buttress plating portion is joined to a lower edge of the basket portion and extends toward a femoral shaft and a posterolateral direction of an intertrochanteric area such that the buttress plating portion is joined to the area.

The lesser trochanter securing device according to the embodiment of the present invention includes: a basket portion covering a lesser trochanter; and a buttress plating portion joined to a lower edge of the basket portion and extending toward a femoral shaft such that the buttress plating portion is mainly secured and joined to the femoral shaft.

Advantageous Effects of Invention

The lesser trochanter securing device according to the embodiment of the present invention can expand the application of the artificial hip joint replacement surgery even to the case of a patient who suffers from the comminuted fracture in the femoral lesser trochanter, which receives the most force, and the surrounding thereof.

In the case of a femoral intertrochanteric fracture in which a lesser trochanter is fractured, an artificial hip joint replacement surgery has been almost impossible in the past. Meanwhile, since the conventional method cannot obtain good results, the application of the artificial hip joint replacement surgery has been almost avoided.

Comminuted fractures may occur in the femoral lesser trochanter and its surrounding, and in particular, the lesser trochanter may be severely damaged by osteoporosis or the like. In this case, since the important basement buttressing the artificial structure has disappeared, the application of the artificial hip joint replacement surgery has been almost impossible till now. In addition, in the case where the surgery is performed in a conventional manner, the stability of the surgery is very low. That is, the artificial joint may be released, the bone may not be attached, or the leg may be shortened. Therefore, the revision surgery has been unavoidable before long.

The lesser trochanter securing device according to the embodiment of the present invention can firmly secure the surrounding of the femoral stem by attaching an anatomically specially designed buttress fixating plate to the lesser trochanter and wrapping or fixing the buttress fixating plate by using a wire or the like.

Therefore, the lesser trochanter securing device can further improve the surgery stability and reliability by applying to the artificial hip joint replacement surgery for the femoral intertrochanteric fracture where the lesser trochanter is separated and fractured. The lesser trochanter securing device can provide a firm fixing force to a fracture area, and can provide a strong basement enough to support a human body's vertical weight even in a surgery for inserting an artificial femoral stem. Therefore, even in the case of a patient whose lesser trochanter fractured, the lesser trochanter securing device can provide the expanded application of the artificial hip joint replacement surgery, remarkably improve ease of surgery to reduce severe complications and sequela, and significantly increase the fixing force of the lesser trochanter area so that a patent can recover quickly and walk early after the artificial hip joint replacement surgery.

Even in a compression hip screw surgery or a gamma nail surgery, the lesser trochanter securing device can be additionally applied to fix the lesser trochanter rapidly strongly and easily.

In addition, in the case of the femoral neck fracture, when an iatrogenic lesser trochanter fracture accidently develops by DR's mistake in the process of replacing the artificial joint, there have been no solutions to stably fix the lesser trochanter fracture. However, when applying to the lesser trochanter fracture, the lesser trochanter securing device easily provides a quick and strong fixation. Therefore, in the case an internal fixation of an intertrochanteric fracture, a substrochanteric fracture, or a proximal femur fracture is required, the lesser trochanter securing device can replace the existing surgical instruments or can be very usefully used as an additional fixation device.

DESCRIPTION OF EMBODIMENTS

A hip joint replacement surgery has been advanced in proportion to the inventions and improvements of artificial prosthesis for hip joint replacement and its application has been expanded.

In the human body, an acetabulum, which is surrounded by a pelvis, or a femoral head, which is a joint part of a femur, can be replaced with an artificial hip joint.

In general, an artificial hip joint is divided into an artificial acetabulum and an artificial femoral head-neck and stem. The artificial acetabulum is made of a metal, polyethylene, or the like, and the artificial femoral head-neck and stem is made of a ceramic, a metal alloy, or the like. The artificial femoral head-neck and stem may be subdivided into an artificial femoral head-neck and an artificial femoral stem. The artificial femoral head is joined to the artificial acetabulum. In general, after cutting the femoral neck above about 1 cm from the lesser trochanter bone, the artificial femoral stem prosthesis is inserted into the femoral medullary canal via the intramedullary canal of the femoral neck.

The artificial hip joint replacement surgery, based on a new invention of an artificial joint and an advanced surgery technique, has recently been widely used because of its high reliability and less sequela.

On the other hand, the hip joint replacement surgery is usually used for the hip joint disease and the fracture of the area around the femoral neck. That is, the hip joint replacement surgery is usually used when there is a fracture damage in the femoral head, the femoral neck, and the acetabulum or when the lesser trochanter is intact. However, when the hip joint replacement surgery is performed on the femoral intertrochanteric fracture, it has been restrictively used in only a part due to very poor or uncertain results and has not been recommended in most cases.

Therefore, when there are lesser trochanter fractures or severely comminuted fractures or when severely displaced fracture fragments are accompanied, the artificial hip joint replacement surgery could not be applied to the femoral intertrochanteric fracture.

In particular, the femoral lesser trochanter area where much force is concentrated is a key point where a weight is concentrated when the artificial femoral stem prosthesis is inserted or before and after the surgery. Therefore, even if there is a slight crack in the lesser trochanter, the artificial hip joint replacement surgery has been contraindicated up to now.

A lesser trochanter securing device according to an embodiment of the present invention attaches a plate having an anatomically designed shape and a size of fracture suitable to the lesser trochanter and the surrounding fracture area. Then, the lesser trochanter securing device is secured to the femur by a wire, a screw, a bone cement, or a fixation within the plate itself. Therefore, the lesser trochanter securing device firmly buttresses the surrounding area of the femoral stem. Therefore, the artificial hip joint replacement surgery can also be stably applied to the severely comminuted and displaced femoral intertrochanteric fracture (including the lesser trochanter fracture), and the like.

The lesser trochanter securing device according to the embodiment of the present invention may secure the fractured lesser trochanter by connecting and wrapping it to the femoral shaft. Therefore, when the artificial hip joint replacement surgery is performed using the lesser trochanter securing device, the artificial femoral stem prosthesis can withstand the weight of the human body because it is secured very firmly. In addition, after the surgery using the lesser trochanter securing device, a patient can regain his/her normal hip joint function and can recover earlier.

On the other hand, when the lesser trochanter is damaged, the conventional fracture surgery, to which the hip joint replacement surgery is not applied, has a problem that since a patient cannot move until the fracture area is completely cured, the recovery is delayed or the occurrence probability of complications or sequela following surgery is higher.

The use of the lesser trochanter securing device according to the embodiment of the present invention further expands the application of the artificial hip joint replacement surgery to even the case where the surgery has been impossible in the past. Therefore, the surgery procedure becomes faster, easier and more stable and accordingly more satisfactory results can be obtained.

Hereinafter, embodiments of the present invention will be described with reference to the accompanying drawings, so as to explain the present invention to the extent that those skilled in the art can easily carry out the technical spirit of the present invention. The same reference numerals are used to refer to the same elements.

Figure 1:
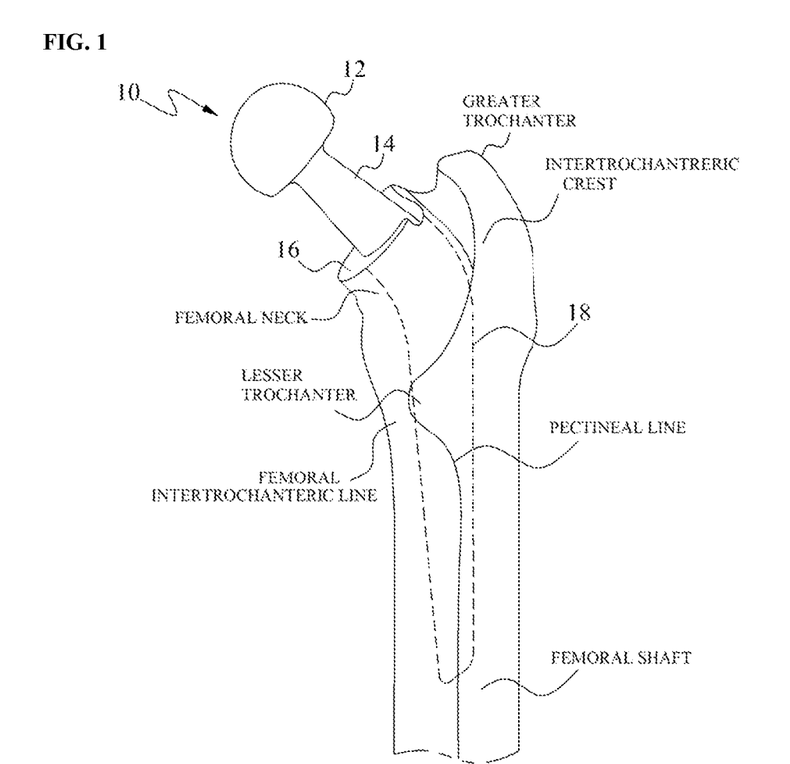
FIG. 1 is a diagram describing a femoral area into which an artificial hip joint is inserted.

FIG. 1 is a diagram describing a femoral area into which an artificial hip joint is inserted.

Referring to FIG. 1, a femoral neck is cut and an artificial femur 10 is inserted into a femoral medullary canal.

The artificial femur 10 includes an artificial femoral head 12, an artificial femoral neck 14, an artificial femoral jaw 16 disposed in the artificial femoral neck 14, and an artificial femoral stem prosthesis 18 extending from the artificial femoral jaw 16 and inserted into the femoral medullary canal.

Figure 2:
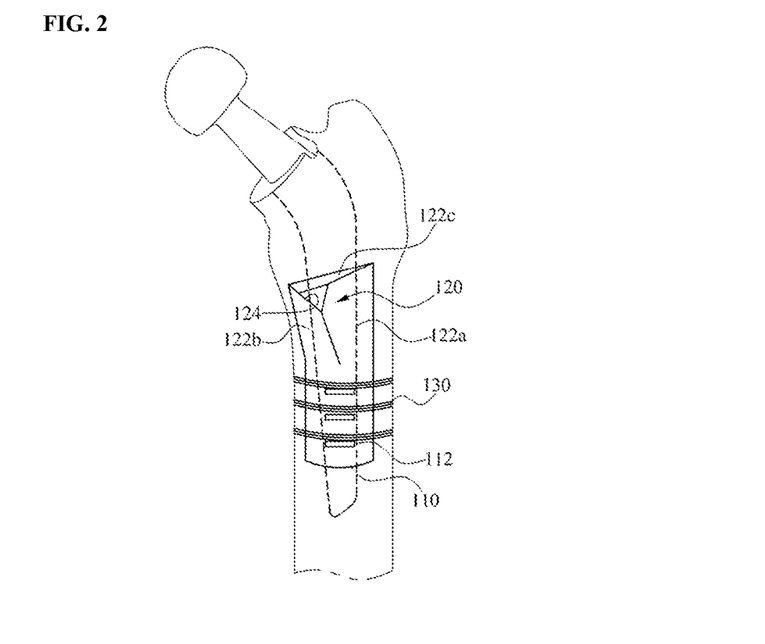
FIG. 2 is a diagram describing a lesser trochanter securing device according to an embodiment of the present invention.

FIG. 2 is a diagram describing a lesser trochanter securing device according to an embodiment of the present invention.

Referring to FIGS. 1 and 2, the lesser trochanter securing device includes a basket portion 120 completely or partially covering the lesser trochanter, and a buttress plating portion 110 joined to a lower edge of the basket portion 120 and extending toward a femoral shaft such that the buttress plating portion 110 is secured and joined to the femoral shaft.

The basket portion 120 covers and buttresses the lesser trochanter. The buttress plating portion 110 is joined to the lower edge of the basket portion 120 and extends toward the femoral shaft, so that the buttress plating portion 110 is anatomically matched with the bone surface of the femoral shaft. In addition, the buttress plating portion 110 is attached to the femoral shaft. The buttress plating portion 110 is secured and joined to the femoral shaft by a wire or the like. The lesser trochanter securing device may have a ladle-like shape. The buttress plating portion 110 may include a body, a wing, and a hump.

The basket portion 120 may have a concave shape. For example, the lesser trochanter may have a triangular pyramid shape or a conical shape. The lesser trochanter may have an anatomically designed shape, a truncated triangular pyramid shape, or a truncated conical shape. The basket portion 120 may be a unit that presses, buttresses and secures the lesser trochanter. Therefore, the damaged lesser trochanter may be completely or partially covered, secured or buttressed to the basket portion 120. The shape of the basket portion 120 may be similar to the shape of the lesser trochanter. An opening 124 may be disposed in a truncated area or a pinnacle of the basket portion 120. Therefore, the basket portion 120 can completely or partially cover the lesser trochanter, without depending on various pinnacle shapes of the lesser trochanter. Hence, the basket portion 120 may preferably have a truncated triangular pyramid shape or a cover shape of an anatomical shape of the lesser trochanter, but is not limited thereto. The basket portion may be modified in various shapes.

A plane connecting the pinnacle of the lesser trochanter, the intertrochanteric line, and the pectineal line may form a first plane, if excluding the pinnacle area of the lesser trochanter. A plane connecting the pinnacle of the lesser trochanter, the pectineal line, and the femoral intertrochanteric line may form a second plane, if excluding the pinnacle area of the lesser trochanter. In addition, a plane connecting the femoral neck from the pinnacle of the lesser trochanter may form a third plane.

The basket portion 120 may include at least one of a first correspondence plane 122*a* corresponding to the first plane, a second correspondence plane 122*b* corresponding to the second plane, and a third correspondence plane 122*c* corresponding to the third plane. The pinnacle area of the lesser trochanter may protrude through the opening 124. The cross section of the opening 124 may be a part of a cutting plane or a triangular shape, based on the anatomical shape of the lesser trochanter, but is not limited thereto. The cross section of the opening 124 may be modified in various shapes. A slope of the second correspondence plane 122*b* may be greater than a slope of the first correspondence plane 122*a*.

The basket portion 120 may be made of any kind of metallic materials or alloys. Preferably, the basket portion 120 may be made of titanium, stainless steel, or a titanium alloy. The material of the basket portion 120 may be modified into or joined to other biocompatible material.

An elastic body (not illustrated) may be disposed inside the basket portion 120. The elastic body may have a truncated conical shell shape. The elastic body may be disposed between the basket portion 120 and the lesser trochanter to provide uniform pressure to the surrounding of the lesser trochanter. The elastic body may be made of silicon or polyethylene. The shape of the elastic body is not limited to the truncated conical shell shape, and may be modified in various shapes as long as it can provide uniform pressure to the surrounding of the lesser trochanter.

The buttress plating portion 110 may be a cylindrical shell having a range of a predetermined azimuthal angle. Alternatively, the buttress plating portion 110 may have a bent plate shape. Therefore, the buttress plating portion 110 may extend in the axial direction of the femoral shaft to cover a part of the femoral shaft. A curvature of the buttress plating portion 110 may be consistent with a curvature of the femoral shaft, and variation and variants may exist according to personal differences.

The buttress plating portion 110 may include a first buttressing curved plane joined to the femoral shaft, and a second buttressing curved plane opposite to the first buttressing curved plane. In the first buttressing curved plane, various kinds of protruding slipping prevention portions (not illustrated) may be disposed in various shapes so as to prevent slipping when the buttress plating portion and the femoral shaft are firmly secured by a circlage wire. The slipping prevention portion may be a unit that prevents the femoral shaft and the buttress plating portion 110 from being slipped each other. The slipping prevention portion may be a unit that protrudes from the first buttressing curved plane and anatomically presses, buttresses and secures the femoral shaft. For example, the slipping prevention portion may have a low rectangular protrusion shape, a cylindrical shape, a gutter or dimple shape, or a wire hole. For example, the wire hole may be formed inside the buttress plating portion 110 in a lateral direction, and the wire passing through the wire hole is wound. In such a manner, the buttress plating portion 110 can be secured to the femoral shaft without slipping.

The buttress plating portion 110 may be secured and joined to the femoral shaft by a fixing unit 130. The fixing unit 130 may include at least one of a wire, a screw, a bone cement, and a fixation within the plate itself. In the case where the buttress plating portion 110 and the femoral shaft are secured using the wire, the buttress plating portion 110 may include at least one hump 112 in the second buttressing curved plane. The hump 112 may firmly fix the wire at a desired position without slipping.

In the case where the buttress plating portion 110 and the femoral shaft are secured using the screw, the buttress plating portion 110 may include at least one through-hole (not illustrated) at a position where there is no latch in the artificial femoral stem insertion portion. The screw may be inserted into the femoral shaft or the lesser trochanter area through the through-hole, while avoiding the artificial femoral stem prosthesis.

In the case where the buttress plating portion 110 and the femoral shaft are secured using the bone cement or adhesive, the bone cement or adhesive may be filled between the buttress plating portion 110 and the femoral shaft.

The buttress plating portion 110 may further include a wing (not illustrated). The wing may extend to the posterolateral direction of the intertrochanteric crest and be joined to the intertrochanteric crest. In the case of the femoral intertrochanteric fracture, the wing may buttress the comminuted fracture fragment of the rear wall. The wing may have an anatomical shape of the intertrochanteric crest such that the wing is closely attached to the intertrochanteric crest.

Figure 3:
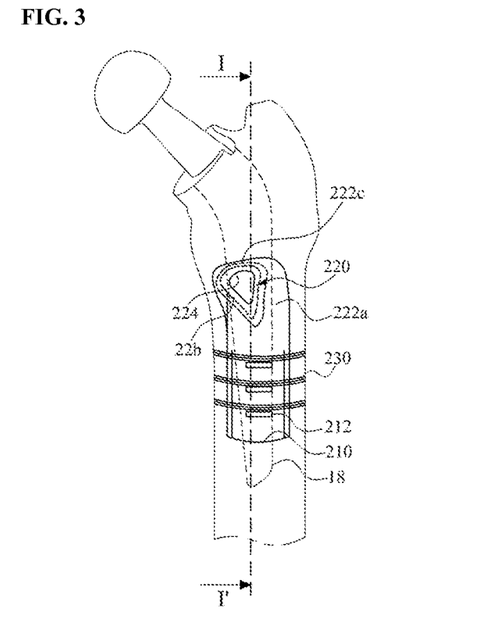
FIG. 3 is a diagram describing a lesser trochanter securing device according to another embodiment of the present invention.
Figure 4:
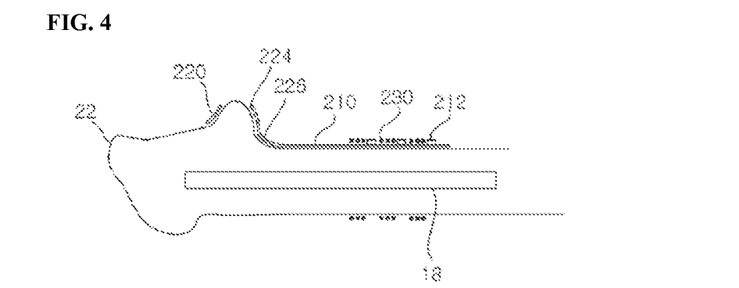
FIG. 4 is a sectional view taken along a femoral shaft direction I-I' in the lesser trochanter securing device of FIG. 3.

FIG. 3 is a diagram describing a lesser trochanter securing device according to another embodiment of the present invention. FIG. 4 is a sectional view taken along a femoral shaft direction I-I' in the lesser trochanter securing device of FIG. 3.

Referring to FIGS. 1, 3 and 4, the lesser trochanter securing device includes a basket portion 220 covering a lesser trochanter, and a buttress plating portion 210 joined to a lower edge of the basket portion 220 and extending toward a femoral shaft such that the buttress plating portion 210 is secured to the femoral shaft. The lesser trochanter securing device may further include an opening 224 disposed at the central region of the basket portion 220.

The basket portion 220 may be variously modified according to the shape of the lesser trochanter. The basket portion 220 may be similar to a conical shell shape that is tapered in an upward direction. The center of the basket portion 220 may be disposed at a position shifted toward a femoral neck.

An opening 224 may be disposed at the pinnacle area of the basket portion 220. The opening 224 may be disposed to be slightly sloped in a femoral diameter direction in the femoral shaft, such that the pinnacle area of the lesser trochanter can protrude.

A plane connecting the pinnacle of the lesser trochanter, the intertrochanteric line, and the pectineal line may form a first plane, if excluding the pinnacle area of the lesser trochanter. In addition, a plane connecting the pinnacle of the lesser trochanter, the pectineal line, and the intertrochanteric line may form a second plane, if excluding the pinnacle area of the lesser trochanter. In addition, a plane connecting the femoral neck from the pinnacle of the lesser trochanter may form a third plane.

The basket portion 220 may include at least one of a first correspondence plane 222a corresponding to the first plane, a second correspondence plane 222b corresponding to the second plane, and a third correspondence plane 222c corresponding to the third plane. The pinnacle area of the lesser trochanter may protrude through the opening 224. The cross section of the opening 224 may have a conical shape, but is not limited thereto. The cross section of the opening 224 may be modified in various shapes.

The basket portion 220 and the buttress plating portion 210 may be joined by a smooth curved plane 226. The buttress plating portion 210 and the femoral shaft may be secured and joined by various fixing units 230. The fixing unit 230 may include at least one of a wire, a screw, a bone cement, and a fixation of the plate itself. In the case where the buttress plating portion 110 and the femoral shaft are secured using the wire, the buttress plating portion 210 may include at least one hump 212 in the second buttressing curved plane. The hump 212 can secure the wire at a desired position and prevent slipping so that the wire is not released.

Figure 5:
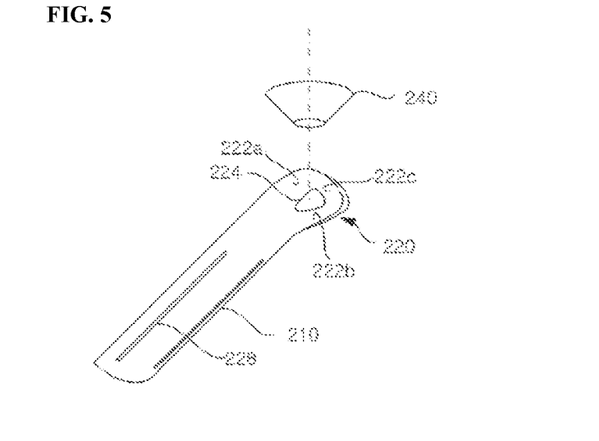
FIGS. 5 and 6 are perspective views describing the lesser trochanter securing device according to another embodiment of the present invention.
Figure 6:
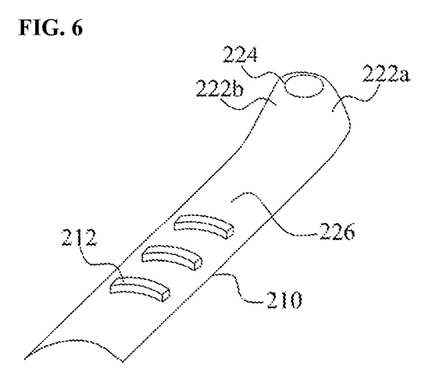

FIGS. 5 and 6 are perspective views describing a lesser trochanter securing device according to another embodiment of the present invention. A description about contents overlapped with those of FIGS. 3 and 4 will be omitted.

Referring to FIGS. 5, 6 and 4, the lesser trochanter securing device includes a basket portion 220 covering a lesser trochanter, and a buttress plating portion 210 joined to a lower edge of the basket portion 220 and extending toward a femoral shaft such that the buttress plating portion 210 is secured and joined to the femoral shaft. The lesser trochanter securing device may further include an opening 224 disposed at the central region of the basket portion 220.

An elastic body 240 may be disposed between the basket portion 220 and the lesser trochanter. Alternatively, the elastic body 240 may be inserted inside the basket portion 220. The elastic body 240 may have a truncated conical shape.

The buttress plating unit 210 may include a slipping prevention unit 228 at the inner surface contacting the femoral shaft. The shape of the slipping prevention unit 228 may be variously modified.

Figure 7:
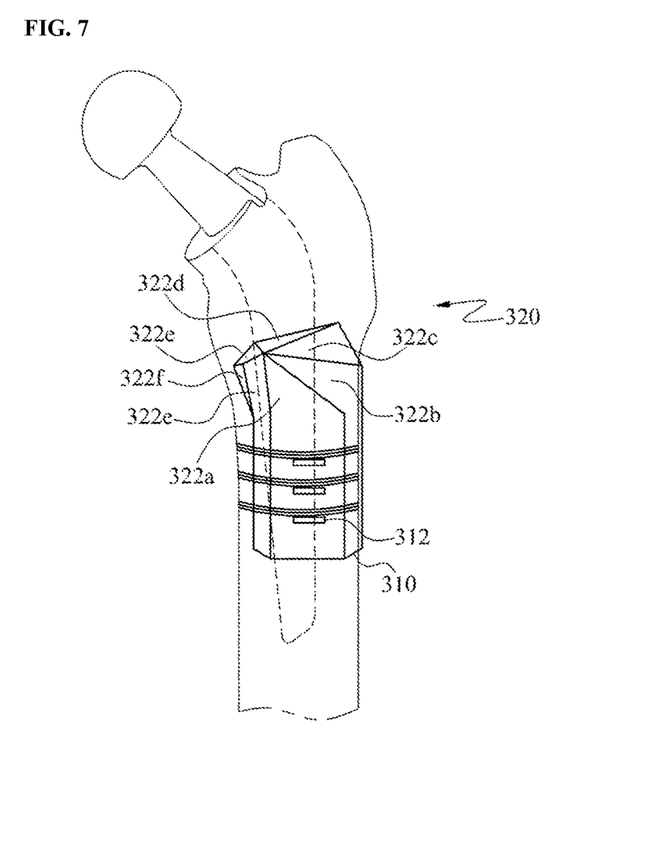
FIGS. 7 and 8 are diagrams describing a lesser trochanter securing device according to other embodiments of the present invention.

FIG. 7 is a diagram describing a lesser trochanter securing device according to still another embodiment of the present invention.

Referring to FIG. 7, the lesser trochanter securing device includes a basket portion 320 covering a lesser trochanter, and a buttress plating portion 310 joined to a lower edge of the basket portion 320 and extending toward a femoral shaft such that the buttress plating portion 310 is secured and joined to the femoral shaft.

The basket portion 320 may be formed by being bent into a plurality of planes. For example, the basket portion 320 may include first to sixth planes 322a to 322e around the pinnacle. A part of the first to sixth planes 322a to 322e may change a plane arrangement relationship, considering the outer shape of the lesser trochanter. Therefore, a part of the first to sixth planes 322a to 322e may be modified considering the outer shape of the lesser trochanter. Although six planes forming the basket portion 320 are taken as an example, the basket portion 320 may be modified without being limited thereto. In addition, the basket portion 320 may include a plane 322f that is not connected to the pinnacle.

The basket portion 320 and the buttress plating portion 310 may be joined by different planes or curved planes. The buttress plating portion 310 may be configured by a plurality of planes or curved planes. The buttress plating portion 310 may extend toward the femoral shaft. The buttress plating portion 310 may be secured and joined to the femoral shaft by the fixing unit 330. The fixing unit 330 may include at least one of a wire, a screw, and a bone cement. In the case where the buttress plating portion 310 and the femoral shaft are secured using the wire, the buttress plating unit 310 may include at least one hump 312 in the second buttressing curved plane. The hump 312 can secure the circlage wire at a desired position without slipping.

Figure 8:
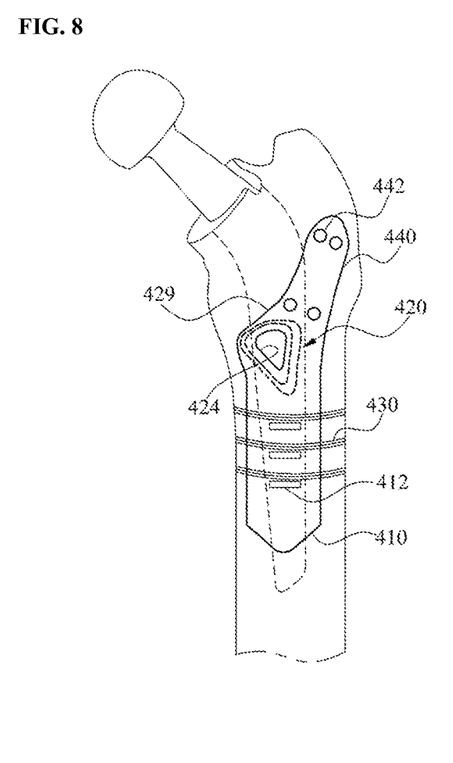

FIG. 8 is a diagram describing a lesser trochanter securing device according to yet another embodiment of the present invention.

Referring to FIG. 8, the lesser trochanter securing device includes a basket portion 420 covering a lesser trochanter, and a buttress plating portion 410 secured and joined to a lower edge of the basket portion 420 and extending toward a femoral shaft such that the buttress plating portion 410 is secured and joined to the femoral shaft. The lesser trochanter securing device may further include an opening 424 disposed at the central region of the basket portion 420.

The buttress plating portion 410 may include a wing 440 extending toward an intertrochanteric crest. The buttress plating portion 410 may extend from a lower edge of the basket portion 420. The wing 440 may extend in the direction of the intertrochanteric crest and connect to the intertrochanteric crest. The wing 440 may have a band shape with a curvature.

In the case of the femoral intertrochanteric fracture, the wing 440 may buttress the comminuted fracture fragment of the rear wall. The wing 440 may have a shape closely attached to the intertrochanteric crest. One end of the wing 440 may be joined to the basket portion 420 or the buttress plating portion 410, and the other end of the wing 440 may extend toward the intertrochanteric crest. At least one circular or oval through-hole 442 may be disposed at the other end of the wing 440. A screw, a wire, or a pin may be secured and joined to the intertrochanteric crest or the greater trochanter through the through-hole 442. In addition, at least one through-hole 429 may be provided at one end of the wing 440 or around the opening 424. The screw, the wire, or the pin may be secured and joined to the lesser trochanter through the through-hole 429.

A hump 412 may be provided in the buttress plating portion 410. A fixing unit 430 may be disposed to cover the femoral shaft, and the slipping of the fixing unit 430 may be prevented by the hump 412 or gutter, the canal, or the like.

The present invention has been described with reference to specific embodiments. It will be understood that various modifications can be made by those skilled in the art, without departing from the scope of the present invention. Therefore, the embodiments should be construed not in restrictive terms but in illustrative terms. The scope of the present invention should be defined by not the above description but the appended claims, and all differences within the equivalents should be construed as falling within the scope of the present invention.

The invention claimed is:

1. A lesser trochanter securing device for use in artificial hip joint replacement, comprising:
   a basket portion adapted to cover, when in use, a lesser trochanter; and
   a buttress plating portion joined to a lower edge of the basket portion and is adapted to extend, when in use, toward a femoral shaft such that the buttress plating portion is secured and joined to the femoral shaft, the basket portion comprising a protrusion extending outward so as to be in conformity with the lesser trochanter when in use,
   wherein the protrusion has a truncated conical shape having first to third planes adapted to cover the lesser trochanter when in use,
   the first plane is disposed in a direction of the femoral shaft with respect to an intertrochanteric line,
   the second plane is disposed in a direction of the femoral shaft to face the first plane, and
   the third plane is disposed toward a femoral neck.

2. The lesser trochanter securing device of claim 1, further comprising an opening provided at a center of the protrusion.

3. The lesser trochanter securing device of claim 1,
   wherein the buttress plating portion further comprises at least one hump formed at the buttress plating portion, and
   the lesser trochanter securing device further comprising a wire capable of wrapping the femoral shaft with the hump.

4. The lesser trochanter securing device of claim 1, further comprising a fixing unit capable of fixing and connecting the buttress plating portion and the femoral shaft.

5. The lesser trochanter securing device of claim 1, wherein the protrusion comprises a plurality of planes adapted to cover the lesser trochanter.

6. The lesser trochanter securing device of claim 1,
   wherein the buttress plating portion further comprises at least one through-hole formed at the buttress plating portion,
   the lesser trochanter securing device further comprising a screw to be inserted into the femoral shaft to be joined to the femoral shaft through the through-hole.

7. The lesser trochanter securing device of claim 1, wherein the buttress plating portion further comprises a wing adapted to extend toward an intertrochanteric crest when in use.

8. An artificial joint for use in hip joint replacement, comprising:
   an artificial femoral stem adapted to be inserted, when in use, into a femoral medullary canal;
   a basket portion adapted to cover a lesser trochanter when in use; and
   a buttress plating portion joined to a lower edge of the basket portion and is adapted to extend, when in use, toward a femoral shaft such that the buttress plating portion is secured and joined to the femoral shaft, the basket portion comprising a protrusion extending outward so as to be in conformity with the lesser trochanter when in use,
   wherein the protrusion has a truncated conical shape having first to third planes adapted to cover the lesser trochanter when in use,
   the first plane is disposed in a direction of the femoral shaft with respect to an intertrochanteric line,
   the second plane is disposed in a direction of the femoral shaft to face the first plane, and
   the third plane is disposed toward a femoral neck.

* * * * *